(12) United States Patent
Garcia Molina (10) Patent No.: US 10,537,704 B2
(45) Date of Patent: Jan. 21, 2020

(54) SYSTEM AND METHOD FOR INCREASING THE RESTORATIVE VALUE OF A NAP

(71) Applicant: KONINKLIJKE PHILIPS N.V., Eindhoven (NL)

(72) Inventor: Gary Nelson Garcia Molina, Madison, WI (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 268 days.

(21) Appl. No.: 15/531,027

(22) PCT Filed: Nov. 24, 2015

(86) PCT No.: PCT/IB2015/059057
§ 371 (c)(1),
(2) Date: May 26, 2017

(87) PCT Pub. No.: WO2016/087983
PCT Pub. Date: Jun. 9, 2016

(65) Prior Publication Data
US 2018/0311462 A1 Nov. 1, 2018

Related U.S. Application Data

(60) Provisional application No. 62/086,934, filed on Dec. 3, 2014.

(51) Int. Cl.
*A61M 21/02* (2006.01)
*A61B 5/00* (2006.01)
(Continued)

(52) U.S. Cl.
CPC ............. *A61M 21/02* (2013.01); *A61B 3/113* (2013.01); *A61B 5/048* (2013.01);
(Continued)

(58) Field of Classification Search
CPC .......... A61M 21/02; A61M 2021/0016; A61M 2021/0027; A61M 2021/0044;
(Continued)

(56) References Cited

U.S. PATENT DOCUMENTS 7,041,049 B1 * 5/2006 Raniere ................. A61M 21/02
128/905
7,593,767 B1 * 9/2009 Modarres ............... A61B 5/048
600/529

(Continued)

FOREIGN PATENT DOCUMENTS

JP 2013162890 A 8/2013
WO 2005055802 A2 6/2005
(Continued)

OTHER PUBLICATIONS

G. Tononi and C. Cirelli, "Sleep function and synaptic homeostasis.," Sleep Med. Rev., vol. 10, No. 1, pp. 49-62, Feb. 2006.
(Continued)

*Primary Examiner* — Navin Natnithithadha
*Assistant Examiner* — Sunita Reddy (57) ABSTRACT

The present disclosure pertains to a system configured to manage a sleep session of a subject. In some embodiments, the sleep session is a nap and the system is configured to increase the restorative value of the nap by enhancing and/or maintaining sleep slow waves (and/or slow wave activity estimated using an EEG) in the subject during the nap with sensory stimuli. The present system is configured to enhance restorative sleep during a nap by delivering sensory stimulation to the subject during lighter NREM sleep stages (e.g., during a portion of stage N2 sleep) while still avoiding arousals. In some embodiments, the system is configured to facilitate a "powernap" by delivering the sensory stimulation
(Continued)

to the subject in such a way so as to prevent transition into deep sleep (e.g., stage N3 sleep).

12 Claims, 6 Drawing Sheets

(51) Int. Cl.
| | |
|---|---|
| A61N 1/36 | (2006.01) |
| A61B 5/0484 | (2006.01) |
| A61B 3/113 | (2006.01) |
| A61B 5/04 | (2006.01) |
| A61B 5/048 | (2006.01) |
| A61B 5/11 | (2006.01) |
| A61M 21/00 | (2006.01) |

(52) U.S. Cl.
CPC ...... *A61B 5/04012* (2013.01); *A61B 5/04845* (2013.01); *A61B 5/1103* (2013.01); *A61B 5/4812* (2013.01); *A61N 1/36078* (2013.01); *A61B 5/4836* (2013.01); *A61M 2021/0016* (2013.01); *A61M 2021/0022* (2013.01); *A61M 2021/0027* (2013.01); *A61M 2021/0044* (2013.01); *A61M 2021/0055* (2013.01); *A61M 2021/0083* (2013.01); *A61M 2205/52* (2013.01); *A61M 2230/10* (2013.01); *A61M 2230/18* (2013.01)

(58) Field of Classification Search
CPC .......... A61M 2205/52; A61M 2230/10; A61M 2230/005; A61M 2021/0083; A61M 2021/0055; A61M 2021/0022; A61M 2230/18; A61N 1/36078; A61B 5/04845; A61B 5/4812; A61B 5/4836; A61B 5/1103; A61B 5/048; A61B 5/04012; A61B 3/113
USPC ...................................... 600/26–28
See application file for complete search history.

(56) References Cited

U.S. PATENT DOCUMENTS

| | | | | |
|---|---|---|---|---|
| 2002/0165462 | A1* | 11/2002 | Westbrook | A61B 5/0205 600/529 |
| 2004/0193068 | A1* | 9/2004 | Burton | A61B 5/0476 600/544 |
| 2005/0076908 | A1* | 4/2005 | Lee | A61B 5/0809 128/204.23 |
| 2005/0283039 | A1* | 12/2005 | Cornel | A61M 21/00 600/27 |
| 2006/0106275 | A1* | 5/2006 | Raniere | A61M 21/02 600/26 |
| 2006/0293608 | A1* | 12/2006 | Rothman | A61B 5/0476 600/545 |
| 2007/0249952 | A1* | 10/2007 | Rubin | A61B 5/0476 600/544 |
| 2008/0081941 | A1 | 4/2008 | Tononi | |
| 2009/0082691 | A1* | 3/2009 | Denison | A61B 5/04004 600/544 |
| 2010/0087701 | A1 | 4/2010 | Berka et al. | |
| 2010/0090798 | A1* | 4/2010 | Garcia Molina | G06K 9/0055 340/5.53 |
| 2011/0238685 | A1* | 9/2011 | Garcia Molina | A61B 5/0476 707/769 |
| 2011/0295083 | A1* | 12/2011 | Doelling | A61B 5/103 600/301 |
| 2012/0238800 | A1* | 9/2012 | Naujokat | A61B 5/0402 600/26 |
| 2012/0251989 | A1* | 10/2012 | Wetmore | G09B 19/00 434/236 |
| 2013/0303837 | A1* | 11/2013 | Berka | A61M 21/02 600/28 |
| 2014/0303428 | A1 | 10/2014 | Berka et al. | |
| 2014/0316192 | A1* | 10/2014 | de Zambotti | A61M 21/02 600/28 |
| 2015/0224017 | A1* | 8/2015 | Graindorge | A61H 23/00 601/46 |
| 2015/0343168 | A1 | 12/2015 | Garcia Molina | |
| 2015/0359482 | A1 | 12/2015 | Garcia Molina et al. | |

FOREIGN PATENT DOCUMENTS

| | | |
|---|---|---|
| WO | 2005084538 A1 | 9/2005 |
| WO | 2009112944 A2 | 9/2009 |
| WO | 2014170881 A1 | 10/2014 |

OTHER PUBLICATIONS

B. A. Riedner, B. K. Hulse, F. Ferrarelli, S. Sarasso, and G. Tononi, "Enhancing sleep slow waves with natural stimuli," Medicamundi, vol. 45, No. 2, pp. 82-88, 2010.

P. Achermann, D. J. Dijk, D. P. Brunner, and A. A. Borbely, "A model of human sleep homeostasis based on EEG slow-wave activity: quantitative comparison of data and simulations.," Brain Res. Bull., vol. 31, No. 1-2, pp. 97-113, Jan. 1993.

A. A. Borbély, "A two process model of sleep regulation.," Hum. Neurobiol., vol. 1, No. 3, pp. 195-204, 1982.

P. Achermann and A. A. Borbély, "Simulation of Human Sleep: Ultradian Dynamics of Electroencephalographic Slow-Wave Activity," J. Biol. Rhythms, vol. 5, No. 2, pp. 141-157, Jun. 1990.

A. A. Borbély and P. Achermann, "Sleep Homeostasis and Models of Sleep Regulation," J. Biol. Rhythms, vol. 14, No. 3, pp. 559-570, Dec. 1999.

Iber, C., Ancoli-Israel, S., Chesson, A. L., & Quan, S. F. (2007). The AASM Manual for the Scoring of Sleep and Associated Events: Rules, Terminology and Technical Specifications. American Academy of Sleep Medicine (First). American Academy of Sleep Medicine.

R. D. McEvoy and L. L. Lack, "Medical staff working the night shift: can naps help?," Med. J. Aust., vol. 185, No. 7, pp. 349-350, Oct. 2006.

K. Susmáková and A. Krakovská, "Discrimination ability of individual measures used in sleep stages classification.," Artif. Intell. Med., vol. 44, No. 3, pp. 261-277, Nov. 2008.

G. Garcia-Molina, M. Bellesi, S. Pastoor, S. Pfundtner, B. A. Riedner, and G. Tononi, "Online Single EEG Channel Based Automatic Sleep Staging," in Engineering Psychology and Cognitive Ergonomics. Applications and Services, D. Harris, Ed. Springer Berlin Heidelberg, 2013, pp. 333-342.

L. De Gennaro, M. Ferrara, F. Ferlazzo, and M. Bertini, "Slow eye movements and EEG power spectra during wake-sleep transition.," Clin. Neurophysiol., vol. 111, No. 12, pp. 2107-2115, Dec. 2000.

Y. Nir, R. J. Staba, T. Andrillon, V. V Vyazovskiy, C. Cirelli, I. Fried, and G. Tononi, "Regional slow waves and spindles in human sleep.," Neuron, vol. 70, No. 1, pp. 153-169, Apr. 2011.

H.-V. V Ngo, J. C. Claussen, J. Born, and M. Mölle, "Induction of slow oscillations by rhythmic acoustic stimulation.," J. Sleep Res., p. 10 pp, Aug. 2012.

Michele Bellesi et al., Frontiers in Systems Neuroscience, Oct. 2, 2014, 2014LTE01133, Title: Enhancement of sleep slow waves: underlying mechanisms and practical consequences Source: http://journal.frontiersin.org/Journal/10.3389/fnsys.2014.00208/pdf.

Michael Czisch et al., PLoS One. 2009; 4(8): e6749. 2014LTE01134, Title: Acoustic Oddball during NREM Sleep: A Combined EEG/fMRI Study Source: http://www.ncbi.nlm.nih.gov/pmc/articles/PMC2727699/.

* cited by examiner

SYSTEM AND METHOD FOR INCREASING THE RESTORATIVE VALUE OF A NAP

CROSS-REFERENCE TO PRIOR APPLICATIONS

This application is the U.S. National Phase application under 35 U.S.C. § 371 of International Application Serial No. PCT/IB2015/059057, filed on 24 Nov. 2015 which claims the benefit of U.S. Provisional Application Ser. No. 62/086,934, filed on 3 Dec. 2014. These applications are hereby incorporated by reference herein.

BACKGROUND

1. Field

The present disclosure pertains to a system and method for increasing the restorative value of a nap.

2. Description of the Related Art

Systems for monitoring sleep are known. Sensory stimulation during sleep is known. Sensory stimulation during sleep is often applied continuously and/or at intervals that do not influence the sleeping patterns of a subject. Sensory stimulation is not typically delivered during naps.

SUMMARY

Accordingly, one or more aspects of the present disclosure relate to a system configured to manage a sleep session of a subject. The system comprises one or more sensory stimulators, one or more sensors, one or more physical computer processors and/or other components. The one or more sensory stimulators are configured to provide sensory stimuli to the subject during the sleep session. The one or more sensors are configured to generate output signals conveying information related to brain activity of the subject. The one or more physical computer processors are configured by computer readable instructions to: determine brain activity parameters of the subject based on the output signals, the brain activity parameters being indicative of sleep stages of the subject; determine the sleep stages of the subject based on the brain activity parameters, the sleep stages including a first sleep stage, a second sleep stage that is deeper than the first sleep stage, and a third sleep stage that is deeper than the first sleep stage and the second sleep stage; predict transitions from the second sleep stage to the third sleep stage based on the brain activity parameters; and control the one or more sensory stimulators to: provide sensory stimulation to the subject responsive to the subject entering the second sleep stage from the first sleep stage; and cease providing sensory stimulation to the subject responsive to a prediction of a transition from the second sleep stage to the third sleep stage indicating that the subject is about to enter the third sleep stage.

Another aspect of the present disclosure relates to a method for managing a sleep session of a subject with a management system. The system comprises one or more sensory stimulators, one or more sensors, one or more physical computer processors, and/or other components. The method comprises: generating, with the one or more sensors, output signals conveying information related to brain activity of the subject; determining, with the one or more physical computer processors, brain activity parameters of the subject based on the output signals, the brain activity parameters being indicative of sleep stages of the subject; determining, with the one or more physical computer processors, the sleep stages of the subject based on the brain activity parameters, the sleep stages including a first sleep stage, a second sleep stage that is deeper than the first sleep stage, and a third sleep stage that is deeper than the first sleep stage and the second sleep stage; predicting, with the one or more physical computer processors, transitions from the second sleep stage to the third sleep stage based on the brain activity parameters; and controlling, with the one or more physical computer processors, the one or more sensory stimulators to: provide sensory stimulation to the subject responsive to the subject entering the second sleep stage from the first sleep stage; and cease providing sensory stimulation to the subject responsive to a prediction of a transition from the second sleep stage to the third sleep stage indicating that the subject is about to enter the third sleep stage.

Still another aspect of present disclosure relates to a system configured to manage a sleep session of a subject. The system comprises means for providing sensory stimuli to the subject during the sleep session; means for generating output signals conveying information related to brain activity of the subject; means for determining brain activity parameters of the subject based on the output signals, the brain activity parameters being indicative of sleep stages of the subject; means for determining the sleep stages of the subject based on the brain activity parameters, the sleep stages including a first sleep stage, a second sleep stage that is deeper than the first sleep stage, and a third sleep stage that is deeper than the first sleep stage and the second sleep stage; means for predicting transitions from the second sleep stage to the third sleep stage based on the brain activity parameters; and means for controlling the means for providing sensory stimulation to: provide sensory stimulation to the subject responsive to the subject entering the second sleep stage from the first sleep stage; and cease providing sensory stimulation to the subject responsive to a prediction of a transition from the second sleep stage to the third sleep stage indicating that the subject is about to enter the third sleep stage.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1:
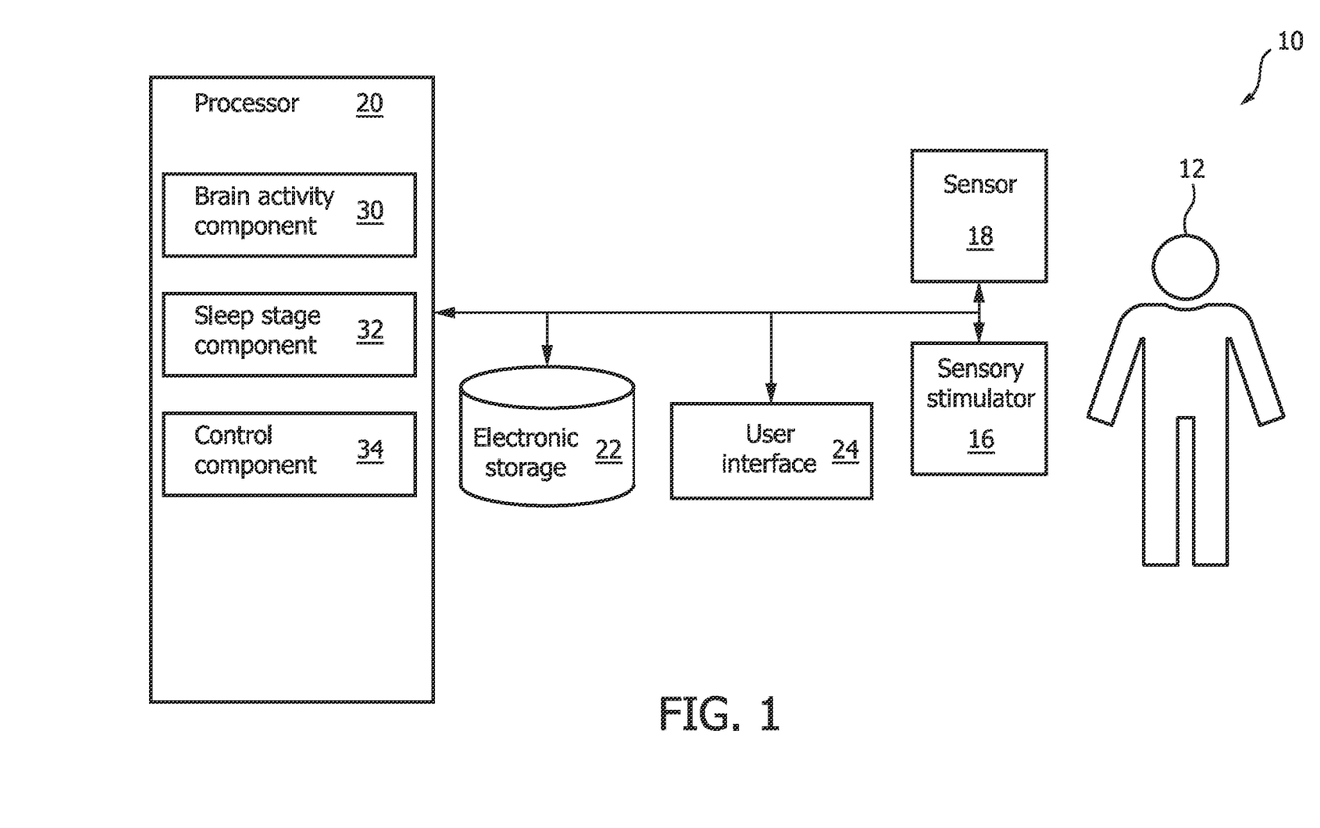
FIG. 1 is a schematic illustration of a system configured to manage a sleep session of a subject.

FIG. 1 is a schematic illustration of a system 10 configured to manage a sleep session of a subject 12. In some embodiments, system 10 includes one or more of a sensory stimulator 16, a sensor 18, a physical computer processor 20, electronic storage 22, a user interface 24, and/or other components. In some embodiments, the sleep session is a nap and system 10 is configured to increase the restorative value of the nap by enhancing and/or maintaining sleep slow waves in subject 12 during the nap with sensory stimuli.

Figure 2:
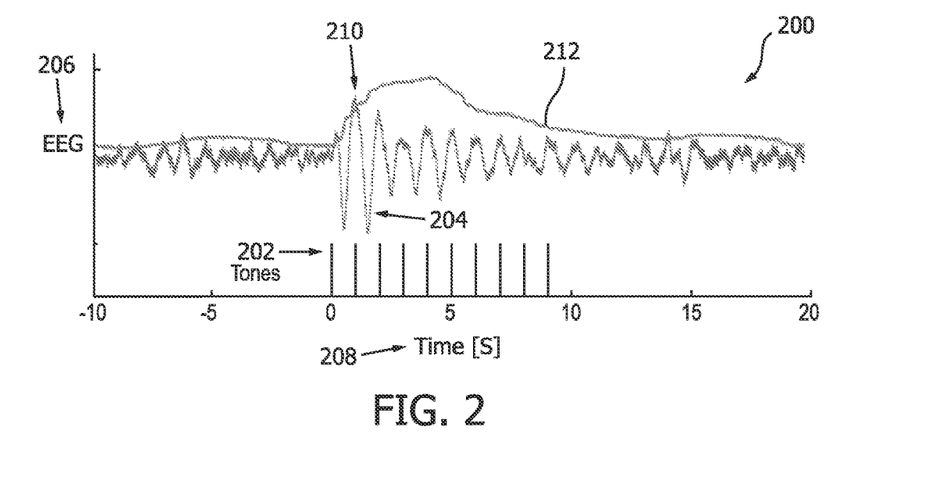
FIG. 2 illustrates enhancement of sleep slow waves that occurs when a sequence of auditory tones is provided to the subject during deep sleep.

FIG. 2 illustrates enhancement 200 of sleep slow waves 204 that occurs when a sequence of auditory tones 202 and/or other sensory stimuli is provided to subject 12 (FIG. 1) during deep sleep (e.g., stage N3 sleep described below). FIG. 2 illustrates an electroencephalogram (EEG) signal 206 over time 208. An increase 210 in the slow wave activity (SWA) curve (e.g., instantaneous EEG power in the 0.5 to 4 Hz band described below) 212 that occurs responsive to the provision of tones 202 (e.g., the individual tones being about 50 milliseconds in length and having a substantially constant inter-tone interval of about 1 second in this example) illustrates the slow wave enhancement effect. The effectiveness of the stimulation 202 is assessed in terms of the SWA because SWA is related to the restorative value of sleep.

Sleep need (or sleep pressure) dissipates by sleeping. The manner in which sleep need dissipation occurs is linked to the temporal dynamics of SWA. SWA has a typical behavior throughout the cyclic variations of a sleep session. SWA builds up during non-rapid eye movement (NREM) sleep, declines before the onset of rapid-eye-movement (REM) sleep, and remains low during REM sleep. The level of SWA for successive NREM cycles gets progressively lower. This is illustrated in FIG. 3.

Figure 3:
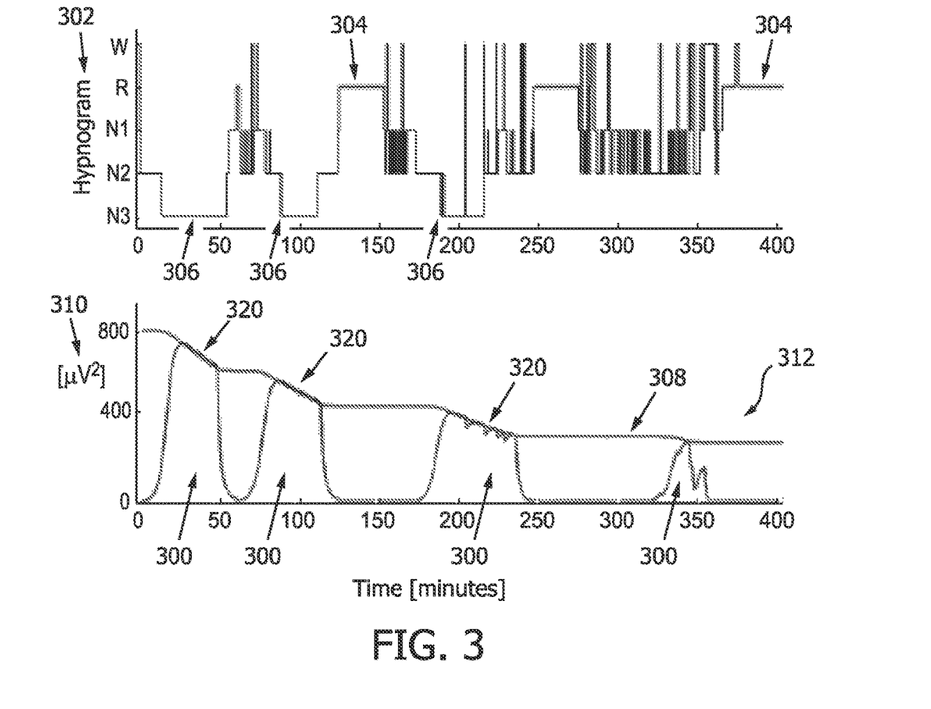
FIG. 3 illustrates slow wave activity, a hypnogram showing REM sleep periods and slow wave sleep periods, and sleep pressure as a function of time during a sleep session.

FIG. 3 illustrates SWA 300, a hypnogram 302 showing REM sleep periods 304 and slow wave sleep periods 306, and sleep pressure as a function of time 308 during a sleep session. Sleep pressure as a function of time 308 decreases from initial sleep pressure 310 to final sleep pressure 312 during the sleep session. FIG. 3 illustrates that sleep pressure as a function of time 308 decreases faster 320 during periods of SWA 300 and/or slow wave sleep 306. The speed at which sleep need dissipates is proportional to SWA in subject 12. This relationship is described in equations (1) and (2) shown below.

$$\frac{dS(t)}{dt} = -\gamma \cdot SWA(t), \tag{1}$$

$$\int_0^t \frac{dS(t)}{dt} dt = -\gamma \cdot \int_0^t SWA(t) dt,$$

$$\Rightarrow S(t) - S_0 = -\gamma \cdot CUMSWA(t), \tag{2}$$

$$\Rightarrow CUMSWA(t) = \frac{S_0 - S(t)}{\gamma}$$

$S(t)$ is the sleep need, $SWA(t)$ is the slow-wave activity at time $t$, and $\gamma$ is a proportionality constant. Taking the integral of both sides in Equation (1) from sleep onset "t=0" to an arbitrary time t results in Equation (2). $S_0$ is the sleep need at the beginning of the sleep session. The summation of the SWA from sleep onset up to a time t is referred to as cumulative SWA or $CUMSWA(t)$. The decrease in sleep need ($S_0$-$S(t)$) after a sleep duration of "t" units of time, is directly proportional to $CUMSWA(t)$. Thus, $CUMSWA(t)$ provides an indication of the restorative value of sleep.

Typically, sensory stimulation is delivered during deep sleep (e.g., stage N3 sleep) to enhance restorative sleep and avoid arousals of subject 12. System 10 is configured to enhance restorative sleep during a nap by delivering sensory stimulation to subject 12 during lighter NREM sleep stages (e.g., during a portion of stage N2 described below) while still avoiding arousals. In some embodiments, system 10 is configured to facilitate a "powernap" by delivering the sensory stimulation to subject 12 in such a way so as to prevent transition into deep sleep (e.g., stage N3 sleep).

Returning to FIG. 1, sensory stimulator 16 is configured to provide sensory stimuli to subject 12. Sensory stimulator 16 is configured to provide sensory stimulation to subject 12 prior to a sleep session, during a sleep session, and/or at other times. For example, sensory stimulator 16 may be configured to provide sensory stimuli to subject 12 to induce deeper sleep in subject 12, maintain sleep in a specific sleep stage (e.g., NREM stage N2 sleep as described below) during the sleep session, during deep (e.g., slow wave sleep) sleep in a sleep session, to facilitate a transition to a lighter stage of sleep, and/or for other reasons and/or at other times. In some embodiments, sensory stimulator 16 may be configured to induce, increase, enhance, maintain, and/or decrease sleep slow waves in subject 12.

Sensory stimulator 16 is configured to facilitate non-invasive brain stimulation and/or other stimulation. Sensory stimulator 16 may be configured to facilitate non-invasive brain stimulation using sensory stimuli. The sensory stimuli include odors, sounds, visual stimulation, touches, tastes, somato-sensory stimulation, haptic, and/or other stimuli. For example, sensory stimulator 16 may be configured to provide acoustic tones to subject 12. Examples of sensory stimulator 16 may include one or more of a music player, a tone generator, a collection of electrodes on the scalp of subject 12, a unit to deliver vibratory stimulation, a coil generating a magnetic field to directly stimulate the brain's cortex, light generators, a fragrance dispenser, and/or other devices. In some embodiments, sensory stimulator 16 is configured to adjust the intensity of the stimulation provided to subject 12.

Sensor 18 is configured to generate output signals conveying information related to brain activity of subject 12. The brain activity of subject 12 may correspond to a current sleep stage of subject 12. The current sleep stage of subject 12 may be associated with rapid eye movement (REM) sleep, non-rapid eye movement (NREM) sleep, and/or other sleep. The current sleep stage of subject 12 may be one or more of NREM stage N1, stage N2, or stage N3 sleep, REM sleep, and/or other sleep stages. Sensor 18 may comprise one or more sensors that measure such parameters directly. For example, sensor 18 may include electroencephalogram (EEG) electrodes configured to detect electrical activity along the scalp of subject 12 resulting from current flows within the brain of subject 12. Sensor 18 may comprise one or more sensors that generate output signals conveying information related to brain activity of subject 12 indirectly. For example, one or more sensors 18 may generate an output based on a heart rate of subject 12 (e.g., sensor 18 may be a heart rate sensor located on the chest of subject 12, and/or be configured as a bracelet on a wrist of subject 12, and/or be located on another limb of subject 12), movement of subject 12 (e.g., sensor 18 may include a bracelet around the wrist and/or ankle of subject 12 with an accelerometer such that sleep may be analyzed using actigraphy signals), respiration of subject 12, and/or other characteristics of subject 12. Although sensor 18 is illustrated at a single location near subject 12, this is not intended to be limiting. Sensor 18 may include sensors disposed in a plurality of locations, such as for example, within (or in communication with) sensory stimulator 16, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may comprise a plurality of processing units. These processing units may be physically located within the same device (e.g., sensory stimulator 16), or processor 20 may represent processing functionality of a plurality of devices operating in coordination.

As shown in FIG. 1, processor 20 is configured to execute one or more computer program components. The one or more computer program components may comprise one or more of a brain activity component 30, a sleep stage component 32, a control component 34, and/or other components. Processor 20 may be configured to execute components 30, 32, and/or 34 by software; hardware; firmware; some combination of software, hardware, and/or firmware; and/or other mechanisms for configuring processing capabilities on processor 20.

It should be appreciated that although components 30, 32, and 34 are illustrated in FIG. 1 as being co-located within a single processing unit, in embodiments in which processor 20 comprises multiple processing units, one or more of components 30, 32, and/or 34 may be located remotely from the other components. The description of the functionality provided by the different components 30, 32, and/or 34 described below is for illustrative purposes, and is not intended to be limiting, as any of components 30, 32, and/or 34 may provide more or less functionality than is described. For example, one or more of components 30, 32, and/or 34 may be eliminated, and some or all of its functionality may be provided by other components 30, 32, and/or 34. As another example, processor 20 may be configured to execute one or more additional components that may perform some or all of the functionality attributed below to one of components 30, 32, and/or 34.

Brain activity component 30 is configured to determine one or more brain activity parameters of subject 12. Brain activity component 30 is configured to determine one or more brain activity parameters based on the output signals from sensor 18 and/or other information. In some embodiments, determining one or more brain activity parameters may include generating and/or monitoring an electroencephalogram (EEG) and/or an electrooculogram (EOG) for a sleep session of subject 12. The EEG and/or EOG may be displayed, for example, by user interface 24. In some embodiments, brain activity component 30 is configured such that the one or more brain activity parameters are, or are related to, a frequency, amplitude, phase, presence of specific sleep patterns such as spindles, K-complexes, sleep slow waves, alpha waves, and/or other characteristics of an EEG and/or EOG signal. In some embodiments, the one or more brain activity parameters are determined based on the frequency, amplitude, and/or other characteristics of the EEG and/or EOG signal. In some embodiments, the determined brain activity parameters and/or the characteristics of the EEG and/or EOG may be and/or indicate sleep states that correspond to the REM and/or NREM sleep stages described herein.

For example, typical EEG characteristics during NREM sleep include a transition from alpha waves (e.g., about 8-12 Hz) to theta waves (e.g., about 4-7 Hz) for sleep stage N1; presence of sleep spindles (e.g., about 11 to 16 Hz) and/or K-complexes (e.g., similar to sleep slow waves) for sleep stage N2; presence of delta waves (e.g., about 0.5 to 2 Hz), also known as sleep slow waves, with peak-to-peak amplitudes greater than about 75 uV for sleep stage N3; and/or other characteristics.

In some embodiments, brain activity component 30 is configured such that determining the brain activity parameters includes determining one or more macro-parameters. The one or more macro-parameters include one or more of a ratio between power in a beta band (about 15-30 Hz) of the EEG signal and power in a delta band (about 0.5-4 Hz) of the EEG signal, a ratio between power in an alpha band (about 8-12 Hz) of the EEG signal and power in a theta band (about 4-7 Hz) of the EEG signal, a ratio between power in a sigma band (about 11-15 Hz) of the EEG signal and the power in the delta band (about 0.5-4 Hz) of the EEG signal, and/or other macro parameters. In general, the one or more macro-parameters may include any ratio between a power in a "fast" (e.g., about 10-50 Hz) frequency band (e.g., beta, sigma, alpha, gamma) of the EEG signal (and/or sub-band where one or both limits are in the 10 to 50 Hz interval such as high alpha 10-12 Hz, beta 15-30 Hz, sigma 11-16 Hz, gamma 30-50 Hz) and power in a "slow" frequency band (e.g., delta, theta) of the EEG signal that can characterize sleep depth during NREM sleep.

In some embodiments, brain activity component 30 is configured such that determining the brain activity parameters includes determining one or more micro-events. The one or more micro-events include one or more of an eye blink, slow eye movements, a spindle, a slow-wave, and/or other micro events. The presence of an eye blink may indicate wakefulness (e.g., with eyes open) in subject 12. Slow eye movements are characteristic of a wake to sleep transition in subject 12. A spindle is typically characteristic of stage N2 sleep. Slow-waves are typically present in stage N3 sleep. K-complexes that are similar in shape are typically present in N2.

Sleep stage component 32 is configured to determine sleep stages in subject 12. The sleep stages are determined based on the output signals, the brain activity parameters, and/or other information. In some embodiments, the sleep stages are determined based on the one or more macro-parameters and the one or more micro-events. In some embodiments, determining the sleep stage is and/or includes detecting sleep stages based on the output signals, the brain activity parameters, the macro-parameters, the micro-events, and/or other information. As described above, the sleep stages of subject 12 may include and/or correspond to one or more of wakefulness, REM sleep, stage N1, stage N2, and/or stage N3 sleep. In some embodiments, slow wave sleep and/or slow wave activity may correspond to stage N3 sleep. In some embodiments, stage N2 and/or stage N3 sleep may be slow wave sleep and/or correspond to slow wave activity. In some embodiments, sleep stage component 32 may determine the sleep stage of subject 12 based on an analysis of the information conveyed by the output signals of sensor 18, the parameters determined by brain activity component 30, and/or other information. The analysis may include monitoring an EEG and/or an EOG for the sleep session of subject 12.

In some embodiments, the analysis may include determining sleep stages based on a slow wave sleep ratio. In some embodiments, the ratio may be:

$$\rho = \log\left(\frac{\beta}{\delta}\right),$$

where (as described above) β and δ represent a power in the beta band (e.g., usually defined as the power in the frequency range 15-30 Hz although variations in limits of the range are very common) of the EEG and a delta band (usually defined as the power in the frequency range 0.5-4.5 Hz although, just as in the case of the beta band, there is no standard definition of the frequency limits) of the EEG respectively. In some embodiments, sleep stage component 32 is configured to determine sleep stages in subject 12 responsive to an instantaneous slow wave sleep ratio ρ(t), estimated based on instantaneous powers β(t) and δ(t), staying below a threshold ratio for longer than a given period of time (e.g., a first threshold/time for stage N2 and a second threshold/time for stage N3). Detecting stage N2 sleep is important in system 10 because detecting N2 sleep indicates that sleep has been initiated (N1 sleep is a transition state) and stimulation is delivered during N2 sleep (described below). In some embodiments, the threshold ratio and/or the given period of time may be determined based on previous sleep sessions of subject 12, and/or other information. In some embodiments, the threshold ratio and/or the given period of time may be programmed at manufacture. (Thresholds are further described below.)

Figure 4:
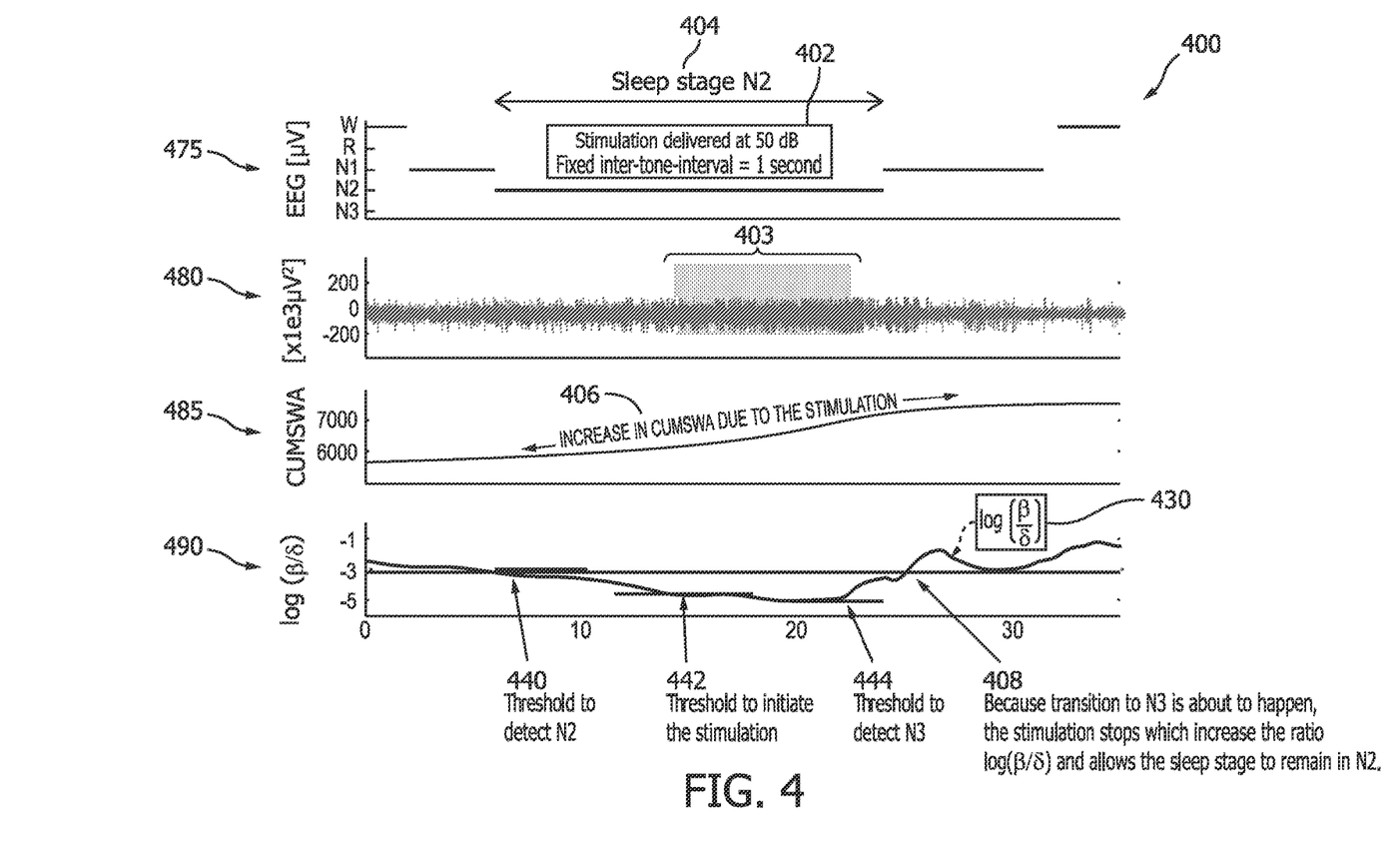
FIG. 4 illustrates information for a 35 minute nap of the subject.

In general, the determined sleep stages may be and/or include at least three sleep stages that include a first sleep stage, a second sleep stage that is deeper than the first sleep stage, and a third sleep stage that is deeper than the first sleep stage and the second sleep stage. In some embodiments, the first, second, and third sleep stages may include and/or correspond to one or more of the sleep stages described above (e.g., wake, REM, NREM stage N1, NREM stage N2, NREM stage N3). For example, in some embodiments, the first sleep stage includes one or more of REM sleep, NREM stage N1 sleep, or a lighter portion of NREM stage N2 sleep. The second sleep stage includes a deeper portion of NREM stage N2 sleep. The third sleep stage includes NREM stage N3 sleep. In this example, stage N2 sleep is subdivided into a lighter portion of NREM stage N2 sleep (included in the first sleep stage) and a deeper portion of NREM stage N2 sleep. In some embodiments, the determined sleep stages may be and/or include more than three sleep stages. For example, the first sleep stage may include N1 and/or other lighter (e.g., REM) sleep stages, the second sleep stage may include the lighter portion of NREM stage N2 sleep, the third sleep stage may include the deeper portion of NREM stage N2 sleep, and a fourth sleep stage may include NREM stage N3 sleep. (This is illustrated in FIG. 4 described further below.)

In some embodiments, sleep stage component 32 is configured to predict sleep stage transitions in subject 12. In some embodiments, predicting sleep stage transitions is and/or includes determining a likelihood that a transition is about to occur. In some embodiments, transitions from the second sleep stage (e.g., the deeper portion of NREM stage 2) to the third sleep stage (e.g., N3) are predicted. In some embodiments, the predictions are based on the brain activity parameters and/or other information. In some embodiments, the sleep stage transitions are predicted based on the one or more macro-parameters and the one or more micro-events and/or other parameters. For example, sleep stage component 32 may be configured to predict that subject 12 is about to enter stage 3 sleep because the log (β/δ) ratio (e.g., a macro-parameter) is approaching and/or has breached a threshold level for log (β/δ) that indicates a transition to stage 3. In some embodiments, the threshold level for log (β/δ) that indicates a transition to stage 3 may be lower than an actual N3 transition detection threshold on log (β/δ). Prediction of a transition may occur responsive to log (β/δ) breaching the indication threshold for about 30 seconds (e.g., the duration of a typical sleep epoch) or more (without breaching the actual transition detection threshold). In some embodiments, sleep stage component 32 makes such predictions in an ongoing manner for a sleep session, at regular time intervals during the sleep session, at intervals programmed at manufacture, and/or at other times. In some embodiments, thresholds on the log beta/delta ratio used to detect N1 to N2, N2 to N3, and/or other sleep stage transitions may be determined using information from previous sleep sessions of subject 12, demographic information for a population of subjects similar to subject 12, calibration sleep sessions, and/or other information.

In some embodiments, sleep stage component 32 is configured to determine one or more arousal levels of subject 12 for the sleep session. The one or more arousal levels may indicate a level of wakefulness in subject 12. The one or more arousal levels may be determined based on the output signals of sensors 18, parameters determined by brain activity component 30, information stored in electronic storage 22, testing performed prior to the sleep session, information received and/or selected via user interface 24, and/or other information. In some embodiments, the one or more arousal levels may be determined based on the analysis of the information related to the EEG and/or EOG. For example, the likelihood for an arousal may be quantified from the EEG power in the beta band in short temporal windows (typically about 1.5 second long, for example). Responsive to the power in the beta band exceeding a predefined threshold, system 10 may decide that an arousal is present. In some embodiments, the beta band power threshold for arousals may be determined based on a previous sleep session of subject 12, based on information related a population of subjects demographically similar to subject 12, and/or based on other information. For example, the beta band power threshold may be determined based on a calibration night of sleep during which the EEG of subject 12 is measured and the statistics of the beta power throughout the sleep session are analyzed to set the threshold. As another example, the beta band power threshold may be determined via a database containing the beta thresholds for a population of subjects. The beta band power threshold for subject 12 may be determined based on demographically matching subject 12 with subjects present in the database.

Control component 34 is configured to control sensory stimulator 16 to provide sensory stimulation to subject 12. In some embodiments, sensory stimulator 16 is controlled to provide sensory stimulation to subject 12 responsive to the subject entering the second sleep stage (e.g., the deeper portion of NREM stage 2) from the first sleep stage (e.g., stage N1 and/or the lighter portion of NREM stage 2). Control component 34 is configured such that controlling sensory stimulator 16 includes determining a timing, a frequency, an intensity, and/or other parameters of the stimulation provided to subject 12. The timing, frequency, intensity, and/or other parameters of the stimulation provided to subject 12 may be controlled to maintain, increase, and/or decrease sleep slow waves, for example, in subject 12 during the sleep session. In some embodiments, control component 34 controls sensory stimulator 16 to deliver sensory stimulation to subject 12 to maintain stage N2 sleep in subject 12 during the sleep session, and/or facilitate transitions between sleep states and/or stages (e.g., when subject 12 is falling asleep and/or when it is time to wake subject 12). The timing, frequency, intensity, and/or other parameter determinations are determined based on previous sleep sessions of subject 12, sleep sessions of a representative group of subjects related to subject 12, may be determined at manufacture, and/or determined by other methods. In some embodiments, control component 34 is configured to control sensory stimulator 16 such that the timing of the sensory stimuli (e.g., auditory tones) comprises a regular, repeating interval of time between individual stimuli delivered to subject 12 and/or may have an irregular interval. By way of a non-limiting example, tone duration may be in the interval from about 50 to about 200 milliseconds. An inter-tone interval between tones may be variable. Typical average inter-tone interval is about 5 seconds, for example. Given such a relatively long average inter-tone interval, the intensity of the tone may be higher (e.g., >50 dB) as compared to what is usually applied in N3 sleep.

In some embodiments, control component 34 controls sensory stimulator 16 to accelerate transitions through sleep stages toward stage N3 sleep. In such embodiments, control component 34 may control sensory stimulator 16 to deliver continuous auditory stimulation, for example. This may optimize the duration of a powernap.

In some embodiments, control component 34 controls sensory stimulator 16 to provide the sensory stimulation during the sleep session such that the sensory stimulation does not unintentionally wake subject 12 and/or cause subject to transition into deep (stage N3) sleep. Controlling sensory stimulator 16 to provide sensory stimulation so subject 12 is not unintentionally aroused from sleep and/or allowed to transition to deep sleep may be accomplished by controlling the timing, frequency, intensity, and/or other parameters of the stimulation. For example, control component 34 may control sensory stimulator 16 to provide the sensory stimulation at a low intensity level when subject 12 is to remain asleep and at a high intensity level if subject 12 is to be aroused from deep sleep. As another example, control component 34 may cause sensory stimulator 16 to deliver acoustic stimulation to subject 12 to increase sleep slow waves just after subject 12 has fallen asleep (e.g., to speed the transition to stage N2 sleep), and not while subject 12 is falling asleep. In some embodiments, sensory stimulator 16 is controlled to cease providing sensory stimulation to subject 12 responsive to a prediction of a transition from the second sleep stage to the third sleep stage indicating that subject 12 is about to enter the third sleep stage. In some embodiments, sensory stimulator 16 is controlled to deliver sensory stimulation to wake subject 12 responsive to the brain activity parameters and/or other information indicating that subject 12 has entered the third sleep stage. In some embodiments, if a possible arousal is detected by system 10 during stimulation and/or before stimulation begins, control component 34 (FIG. 1) controls a sensory stimulator 16 such that any ongoing stimulation stops and/or an onset of stimulation is delayed.

FIG. 4 illustrates information for a 35 minute nap 400 of subject 12 (FIG. 1). FIG. 4 illustrates a hypnogram 475 for the nap, the EEG signal 480, the effect of sensory stimulation on the cumulative SWA (CUMSWA) 485, and/a log of the EEG beta power/delta power ratio curve 490 (e.g. a parameter determined by brain activity component 30 shown in FIG. 1). During the nap, sensory stimulation is delivered 402 (e.g., via sensory stimulator 16 controlled by control component 34 shown in FIG. 1) during a deeper portion 403 of sleep stage N2 404 to enhance SWA and consequently increase 406 the CUMSWA, which enhances the sleep-need dissipation (as shown in Equation 2 above). CUMSWA increases more rapidly when the stimulation is applied. If the SWA increase is such that transition into N3 is predicted/likely (e.g., as determined by sleep stage component 32 shown in FIG. 1), the stimulation is ceased 408.

As shown in FIG. 4, system 10 (FIG. 1) may be configured such that transitions between sleep stages are determined based on a log of an EEG beta power/delta power ratio 430. In some embodiments, sleep stages may be determined (by sleep stage component 32 shown in FIG. 1) based on breaches of log beta/delta thresholds 440, 442, and 444. In FIG. 4, for example, a transition from sleep stage N1 to sleep stage N2 (e.g., a lighter portion of sleep stage N2) is detected responsive to a breach of threshold 440. A transition (e.g., from the lighter portion of stage N2) to a deeper portion of stage N2 is detected responsive to a breach of threshold 442. A transition to sleep stage N3 would be detected responsive to a breach of threshold 444. In FIG. 4, sensory stimulation 402 is delivered once the transition to the deeper portion of sleep stage N2 is detected (e.g., responsive to breaching threshold 442) and ceased 408 because a transition into N3 is predicted.

In some embodiments, the thresholds may correspond to traditional transitions between sleep stages (wake, REM, N1, N2, and N3). In some embodiments, (e.g., as shown in FIG. 4), one or more thresholds may correspond to transitions between portions of an individual sleep stage (e.g., a transition between a lighter portion of N2 and a deeper portion of N2). In some embodiments, the thresholds may be programmed at manufacture, set by a user via user interface 24 (e.g., and received by sleep stage component 32 shown in FIG. 1), determined (e.g., by sleep stage component 32) based on previous sleep of subject 12, and/or determined by other methods. The present disclosure contemplates that the thresholds may be subject independent (e.g., programmed at manufacture based on a population of previously tested subjects) and/or may be subject specific (e.g., determined for subject 12 based on previous sleep sessions of subject 12). In some embodiments, sleep stage component 32 may be configured to learn and/or adjust the thresholds over time based on the sleep sessions of subject 12.

The description of log beta/delta and the thresholds thereon are not intended to be limiting. System 10 may be configured to determine sleep stages based on thresholds and/or any other distinguishing features for any parameter that allows system 10 (FIG. 1) to function as described herein.

Figure 5:
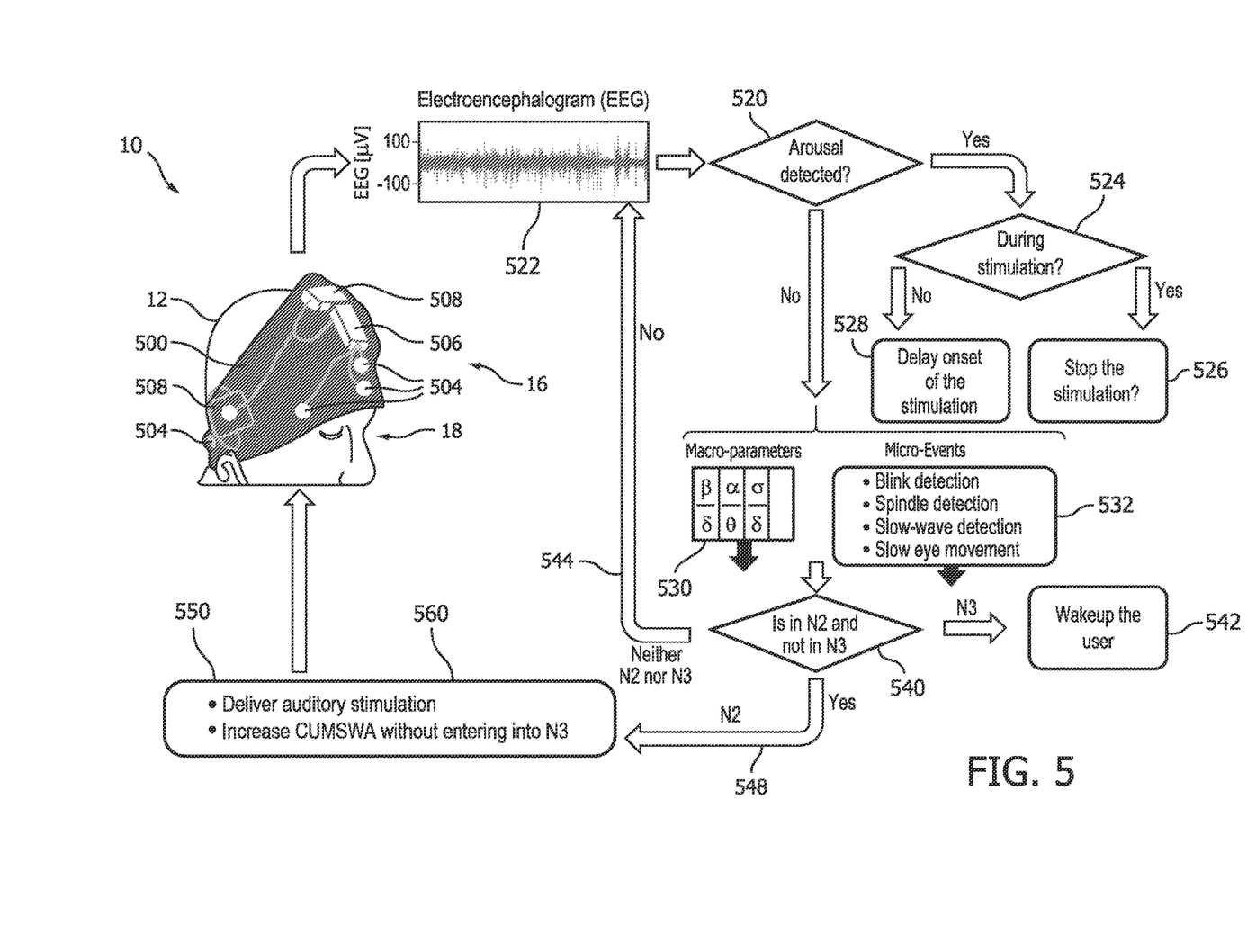
FIG. 5 illustrates an example of the system in operation.

FIG. 5 illustrates an example of system 10 in operation. FIG. 5 illustrates delivering sensory stimulation 550 to increase cumulative SWA (CUMSWA) without causing subject 12 to enter stage N3 sleep 560. FIG. 5 illustrates a headband 500 worn by subject 12 and that includes sensing electrodes 504, a bio-signal amplifier 506, and a wireless audio device 508. Sensing electrodes 504 and bio-signal amplifier 506 may be represented, for example, by sensor 18 in FIG. 1. Wireless audio device 508 may be represented, for example, by sensory stimulator 16 shown in FIG. 1. Possible arousal events 520 are detected based on EEG signals 522 (e.g., output signals from sensor 18). If a possible arousal is detected by system 10 during stimulation 524, control component 34 (FIG. 1) controls a sensory stimulator 16 such that any ongoing stimulation stops 526 and/or an onset of stimulation is delayed 528. If no arousal is detected, macro-parameters 530, micro-events 532 (determined by brain activity component 30 shown in FIG. 1) and/or other parameters are used to determine 540 the sleep stage (e.g., REM, NREM stage N1, the lighter part of N2, the deeper part of N2, N3) of subject 12. If deep sleep (N3) is detected, the auditory stimulation is delivered 542 to wake subject 12. If neither stage N3 or N2 (e.g., the deeper portion of stage N2) is detected 544, no sensory stimulation is delivered and the EEG signal 522 continues to be monitored. Responsive to detection 548 of stage N2 and/or, for example, the deeper portion of stage N2 described above, sensory stimulation 550 is delivered to subject 12 to increase cumulative SWA (CUMSWA) without causing subject 12 to enter stage N3 sleep 560.

Figure 6A:
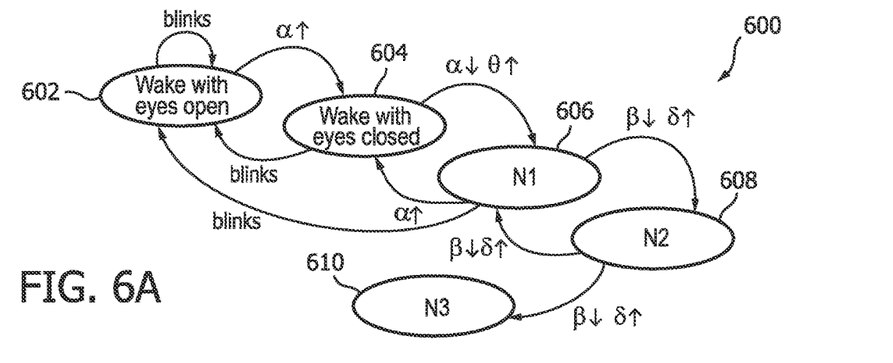
FIG. 6A illustrates a progression through sleep stages in the subject during a nap.
Figure 6B:
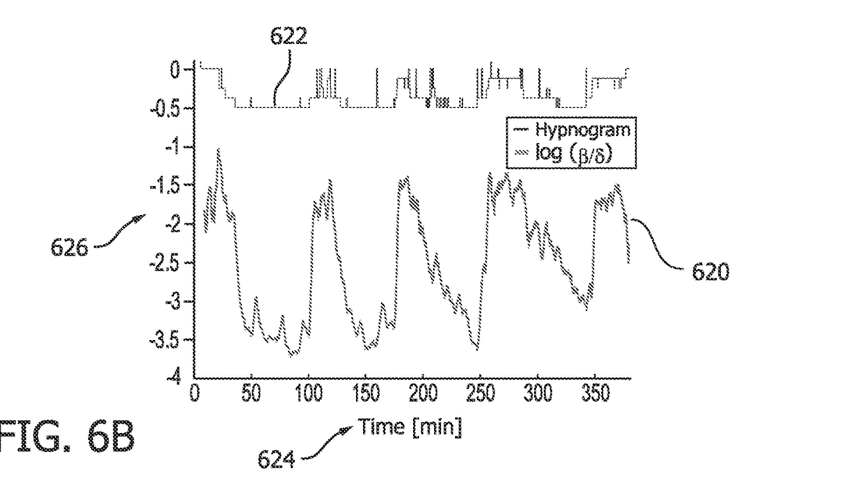
FIG. 6B illustrates how the log beta/delta ratio very closely follows a hypnogram over time for the nap.
Figure 6C:
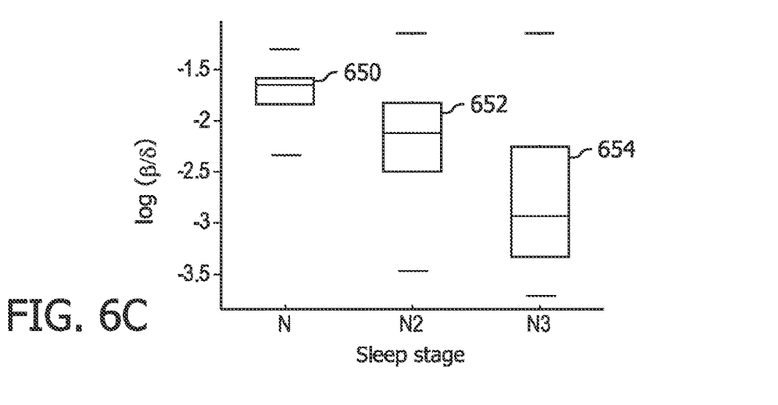
FIG. 6C shows boxplots for sleep stages N1, N2, and N3 of the log beta/delta ratio.

FIG. 6A illustrates a progression through sleep stages 602, 604, 606, 608, 610 in a subject (e.g., subject 12 shown in FIG. 1) during a nap (a sleep session). During the nap, system 10 (FIG. 1) detects sleep stage N2 with high specificity (e.g., >0.8) and a reasonable sensitivity (e.g., >0.7). A state machine approach 600 to detecting stage N2 sleep is illustrated in FIG. 6A. The initial state 602 in this model is "wake with eyes open". System 10 continues to determine that subject 12 in this initial state for as long as eye blinks are detected. When eye-blinks are no longer detected and the power in the alpha band increases (alpha waves are present in the EEG), system 10 determines that subject 12 has transitioned into the second state 604 "wake with eyes closed". If the power in the alpha band decreases and the power in the theta band increases, system 10 determines that subject 12 has transitioned into N1 sleep 606. To detect N2 608 and N3 610, the log of the power ratio beta/delta is used. FIG. 6B illustrates how the log beta/delta 620 ratio very closely follows the hypnogram 622 over time 624 for the nap 626. FIG. 6C shows boxplots 650, 652, 654 for sleep stages N1, N2, and N3 of the log beta/delta ratio. The boxplots illustrate the distribution of the log beta/delta ratio for NREM sleet-sleep stages N1, N2, and N3 and how thresholds on log beta/delta may be used to determine sleep stages in subject 12. In some embodiments, the threshold to detect an N1 to N2 transition is set to about −1.75 and the threshold to detect an N2 to N3 transition is set to about −2.5.

Figure 7:
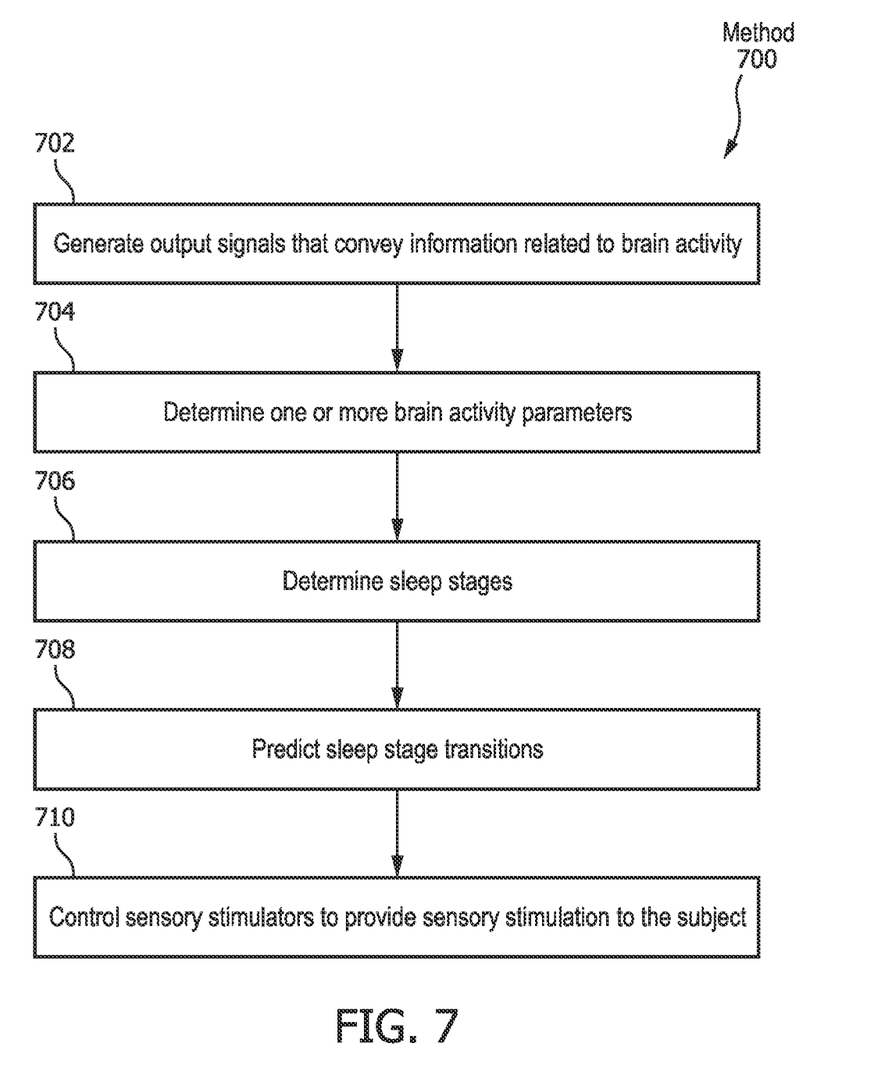
FIG. 7 illustrates a method for managing a sleep session of a subject.

FIG. 7 illustrates a method 700 for a method for managing a sleep session of a subject with a management system. The system comprises one or more sensory stimulators, one or more sensors, one or more physical computer processors, and/or other components. The one or more physical computer processors are configured to execute computer program components. The computer program components comprise a brain activity component, sleep stage component, a control component, and/or other components. The operations of method 700 presented below are intended to be illustrative. In some embodiments, method 700 may be accomplished with one or more additional operations not described, and/or without one or more of the operations discussed. Additionally, the order in which the operations of method 700 are illustrated in FIG. 7 and described below is not intended to be limiting.

In some embodiments, method 700 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 700 in response to instructions stored electronically on an electronic storage medium. The one or more processing devices may include one or more devices configured through hardware, firmware, and/or software to be specifically designed for execution of one or more of the operations of method 700.

At an operation 702, output signals conveying information related to brain activity are generated. In some embodiments, the output signals are generated during a nap of the subject. In some embodiments, system 10 may be configured to generate an EEG based on the output signals. In some embodiments, operation 702 is performed by one or more sensors the same as or similar to sensors 18 (shown in FIG. 1 and described herein).

At an operation 704, one or more brain activity parameters are determined. In some embodiments, the brain activity parameters may be determined based on the EEG, the output signals, and/or other information. In some embodiments, the brain activity parameters are indicative of sleep stages of the subject. In some embodiments, determining the brain activity parameters includes determining one or more macro-parameters. The one or more macro-parameters include one or more of a ratio between power in a beta band of the EEG signal and power in a delta band of the EEG signal, a ratio between power in an alpha band of the EEG signal and power in a theta band of the EEG signal, a ratio between power in a sigma band of the EEG signal and the power in the delta band of the EEG signal, a ratio between power in a fast frequency band of the EEG signal and power in a slow frequency band of the EEG signal, and/or other parameters. In some embodiments, determining the brain activity parameters includes determining one or more micro-events. The one or more micro-events include one or more of an eye blink, slow eye movements, a spindle, a slow-wave, and/or other micro events. In some embodiments, operation 704 is performed by a processor component the same as or similar to brain activity component 30 (shown in FIG. 1 and described herein).

At an operation 706, sleep stages of the subject are determined. The sleep stages are determined based on the brain activity parameters. The sleep stages include a first sleep stage, a second sleep stage that is deeper than the first sleep stage, and a third sleep stage that is deeper than the first sleep stage and the second sleep stage. In some embodiments, the first sleep stage includes one or more of REM sleep, NREM stage N1 sleep, or a lighter portion of NREM stage N2 sleep. The second sleep stage includes a deeper portion of NREM stage N2 sleep. The third sleep stage includes NREM stage N3 sleep. In some embodiments, the sleep stages are determined based on the one or more macro-parameters and the one or more micro-events. In some embodiments, operation 706 is performed by a processor component the same as or similar to sleep stage component 32 (shown in FIG. 1 and described herein).

At an operation 708, sleep stage transitions in the subject are predicted. In some embodiments, transitions from the second sleep stage to the third sleep stage are predicted. In some embodiments, the predictions are based on the brain activity parameters and/or other information. In some embodiments, the sleep stage transitions are predicted based on the one or more macro-parameters and the one or more micro-events. In some embodiments, operation 708 is performed by a processor component the same as or similar to sleep stage component 32 (shown in FIG. 1 and described herein).

At an operation 710, the sensory stimulators are controlled to provide sensory stimulation to the subject. In some embodiments, the sensory stimulators are controlled to provide sensory stimulation to the subject responsive to the subject entering the second sleep stage from the first sleep stage. In some embodiments, the sensory stimulators are controlled to cease providing sensory stimulation to the subject responsive to a prediction of a transition from the second sleep stage to the third sleep stage indicating that the subject is about to enter the third sleep stage. In some embodiments, the one or more sensory stimulators are controlled to deliver sensory stimulation to wake the subject responsive to the brain activity parameters indicating that the subject has entered the third sleep stage. In some embodiments, operation 710 is performed by a processor component the same as or similar to control component 34 (shown in FIG. 1 and described herein).

Returning to FIG. 1, electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via user interface 24 and/or external computing systems, and/or other information that enables system 10 to function properly. Electronic storage 22 may be (in whole or in part) a separate component within system 10, or electronic storage 22 may be provided (in whole or in part) integrally with one or more other components of system 10 (e.g., processor 20).

User interface 24 is configured to provide an interface between system 10 and subject 12, and/or other users through which subject 12 and/or other users may provide information to and receive information from system 10 (e.g., a target sleep stage). This enables data, cues, results, and/or instructions and any other communicable items, collectively referred to as "information," to be communicated between a user (e.g., subject 12) and one or more of sensory stimulator 16, sensor 18, processor 20, and/or other components of system 10. For example, an EEG may be displayed to a caregiver via user interface 24.

Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, user interface 24 comprises a plurality of separate interfaces. In some embodiments, user interface 24 comprises at least one interface that is provided integrally with sensory stimulator 16 and/or other components of system 10.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to manage a sleep session of a subject, the system comprising:
one or more sensory stimulators configured to provide sensory stimuli to the subject during the sleep session;
one or more sensors configured to generate output signals conveying information related to brain activity of the subject; and
one or more physical computer processors configured by computer readable instructions to:
determine brain activity parameters of the subject based on the output signals, the brain activity parameters being indicative of sleep stages of the subject;
determine the sleep stages of the subject based on the brain activity parameters, the sleep stages including a first sleep stage, a second sleep stage that is deeper than the first sleep stage, and a third sleep stage that is deeper than the first sleep stage and the second sleep stage,
wherein the first sleep stage includes one or more of REM sleep, NREM stage N1 sleep, or a lighter portion of NREM stage N2 sleep, the second sleep stage includes a deeper portion of NREM stage N2 sleep, and the third sleep stage includes NREM stage N3 sleep;
predict a transition from the second sleep stage to the third sleep stage based on the brain activity parameters; and
control the one or more sensory stimulators to:
provide sensory stimulation to the subject responsive to the subject entering the second sleep stage from the first sleep stage; and
cease providing the sensory stimulation to the subject responsive to the prediction of the transition from the second sleep stage to the third sleep stage indicating that the subject is about to enter the third sleep to prevent a transition to deep sleep.

2. The system of claim 1, wherein the sleep session is a nap.

3. The system of claim 1, wherein the one or more sensors are configured such that the output signals include an EEG signal,
wherein the one or more physical computer processors are configured such that determining the brain activity parameters includes:
determining one or more macro-parameters, the one or more macro-parameters including one or more of a ratio between power in a beta band of the EEG signal and power in a delta band of the EEG signal, a ratio between power in an alpha band of the EEG signal and power in a theta band of the EEG signal, a ratio between power in a sigma band of the EEG signal and the power in the delta band of the EEG signal, or a ratio between power in a fast frequency band of the EEG signal and power in a slow frequency band of the EEG signal; and
determining one or more micro-events, the one or more micro-events including one or more of an eye blink, slow eye movements, a spindle, or a slow-wave; and wherein the one or more physical computer processors are configured such that sleep stages are determined based on the one or more macro-parameters and the one or more micro-events.

4. The system of claim 1, wherein the one or more physical computer processors are configured to control the one or more sensory stimulators to deliver waking sensory stimulation to wake the subject responsive to the brain activity parameters indicating that the subject has entered the third sleep stage.

5. A method for managing a sleep session of a subject with a management system, the system comprising one or more sensory stimulators, one or more sensors, and one or more physical computer processors, the method comprising:
generating, with the one or more sensors, output signals conveying information related to brain activity of the subject;
determining, with the one or more physical computer processors, brain activity parameters of the subject based on the output signals, the brain activity parameters being indicative of sleep stages of the subject;
determining, with the one or more physical computer processors, the sleep stages of the subject based on the brain activity parameters, the sleep stages including a first sleep stage, a second sleep stage that is deeper than the first sleep stage, and a third sleep stage that is deeper than the first sleep stage and the second sleep stage;
wherein the first sleep stage includes one or more of REM sleep, NREM stage N1 sleep, or a lighter portion of NREM stage N2 sleep, the second stage includes a deeper portion of NREM stage N2 sleep, and the third sleep stage includes NREM stage N3 sleep;
predicting, with the one or more physical computer processors, a transition from the second sleep stage to the third sleep stage based on the brain activity parameters; and
controlling, with the one or more physical computer processors, the one or more sensory stimulators to:
provide sensory stimulation to the subject responsive to the subject entering the second sleep stage from the first sleep stage; and
cease providing the sensory stimulation to the subject responsive to the prediction of the transition from the second sleep stage to the third sleep stage indicating that the subject is about to enter the third sleep stage to prevent a transition to deep sleep.

6. The method of claim 5, wherein the sleep session is a nap.

7. The method of claim 5, wherein the output signals include an EEG signal,
wherein determining the brain activity parameters includes:
determining one or more macro-parameters, the one or more macro-parameters including one or more of a ratio between power in a beta band of the EEG signal and power in a delta band of the EEG signal, a ratio between power in an alpha band of the EEG signal and power in a theta band of the EEG signal, a ratio between power in a sigma band of the EEG signal and the power in the delta band of the EEG signal, or a ratio between power in a fast frequency band of the EEG signal and power in a slow frequency band of the EEG signal; and determining one or more micro-events, the one or more micro-events including one or more of an eye blink, slow eye movements, a spindle, or a slow-wave; and wherein the sleep stages are determined based on the one or more macro-parameters and the one or more micro-events.

8. The method of claim 5, wherein the one or more sensory stimulators are controlled to deliver waking sensory stimulation to wake the subject responsive to the brain activity parameters indicating that the subject has entered the third sleep stage.

9. A system configured to manage a sleep session of a subject, the system comprising:

means for providing sensory stimuli to the subject during the sleep session;

means for generating output signals conveying information related to brain activity of the subject;

means for determining brain activity parameters of the subject based on the output signals, the brain activity parameters being indicative of sleep stages of the subject;

means for determining the sleep stages of the subject based on the brain activity parameters, the sleep stages including a first sleep stage, a second sleep stage that is deeper than the first sleep stage, and a third sleep stage that is deeper than the first sleep stage and the second sleep stage, wherein the first sleep stage includes one or more of REM sleep, NREM stage N1 sleep, or a lighter portion of NREM stage N2 sleep, the second sleep stage includes a deeper portion of N2 sleep, and the third sleep stage includes NREM stage N3 sleep;

means for predicting a transition from the second sleep stage to the third sleep stage based on the brain activity parameters; and means for controlling the means for providing sensory stimulation to:

provide sensory stimulation to the subject responsive to the subject entering the second sleep stage from the first sleep stage; and cease providing the sensory stimulation to the subject responsive to the prediction of the transition from the second sleep stage to the third sleep stage indicating that the subject is about to enter the third sleep stage to prevent a transition to deep sleep.

10. The system of claim 9, wherein the sleep session is a nap.

11. The system of claim 9, wherein the output signals include an EEG signal, wherein determining the brain activity parameters includes:

determining one or more macro-parameters, the one or more macro-parameters including one or more of a ratio between power in a beta band of the EEG signal and power in a delta band of the EEG signal, a ratio between power in an alpha band of the EEG signal and power in a theta band of the EEG signal, a ratio between power in a sigma band of the EEG signal and the power in the delta band of the EEG signal, or a ratio between power in a fast frequency band of the EEG signal and power in a slow frequency band of the EEG signal; and determining one or more micro-events, the one or more micro-events including one or more of an eye blink, slow eye movements, a spindle, or a slow-wave; and wherein sleep stages are determined based on the one or more macro-parameters and the one or more micro-events.

12. The system of claim 9, wherein the means for providing sensory stimulation are controlled to deliver waking sensory stimulation to wake the subject responsive to the brain activity parameters indicating that the subject has entered the third sleep stage.

\* \* \* \* \*